US00PP15494P2

(12) United States Plant Patent
Brown

(10) Patent No.: US PP15,494 P2
(45) Date of Patent: Jan. 25, 2005

(54) ***PETUNIA* PLANT NAMED 'MP201'**

(50) Latin Name: *Petunia×hybrida*
Varietal Denomination: MP201

(75) Inventor: Graham Noel Brown, Pennant Hills (AU)

(73) Assignee: Nuflora International Pty. Ltd., Macquarie Fields (AU)

( * ) Notice: Subject to any disclaimer, the term of this patent is extended or adjusted under 35 U.S.C. 154(b) by 0 days.

(21) Appl. No.: 10/820,503

(22) Filed: Apr. 7, 2004

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—C. A. Whealy

(57) ABSTRACT

A new and distinct cultivar of *Petunia* plant named 'MP201', characterized by its compact, mounded and outwardly spreading plant habit; freely branching habit; and numerous small dark blue violet-colored flowers.

1 Drawing Sheet

Botanical classification: *Petunia×hybrida* cultivar MP201.

BACKGROUND OF THE INVENTION

The present Invention relates to a new and distinct cultivar of *Petunia* plant, botanically known as *Petunia×hybrida*, and hereinafter referred to by the cultivar name MP201.

The new *Petunia* is a product of a planned breeding program conducted by the Inventor in Cobbitty, New South Wales, Australia. The objective of the breeding program is to create outwardly spreading *Petunias* with numerous small flowers with attractive flower colors.

The new *Petunia* originated from a cross-pollination made by the Inventor in 2001 of a proprietary *Petunia* selection identified as X99.26.1, not patented, as the female, or seed parent, with a proprietary *Petunia* selection identified as X99.3.11, not patented, as the male, or pollen parent. The new *Petunia* was selected as a single plant from the resulting progeny of the cross-pollination by the Inventor in a controlled environment in Cobbitty, New South Wales, Australia in 2002.

Asexual reproduction of the new cultivar by vegetative cuttings taken in Cobbitty, New South Wales, Australia since December, 2002, has shown that the unique features of this new *Petunia* are stable and reproduced true to type in successive generations.

SUMMARY OF THE INVENTION

Plants of the cultivar MP201 have not been observed under all possible environmental conditions. The phenotype may vary somewhat with variations in environment such as temperature and light intensity without, however, any variance in genotype.

The following traits have been repeatedly observed and are determined to be the unique characteristics of 'MP201'. These characteristics in combination distinguish 'MP201' as a new and distinct cultivar:

1. Compact, mounded and outwardly spreading plant habit.
2. Freely branching habit.
3. Numerous small dark blue violet-colored flowers.

Compared to plants of the female parent selection, plants of the new *Petunia* have smaller flowers. Plants of the new *Petunia* differ from plants of the male parent selection in flower color as plants of the male parent selection have violet-colored flowers.

Plants of the new *Petunia* can be compared to plants of the cultivar Surfinia Blue Violet, not patented. In side-by-side comparisons conducted in Cobbitty, New South Wales, Australia, plants of the new *Petunia* differed from plants of the cultivar MP201 in the following characteristics:

1. Plants of the new *Petunia* were more compact than plants of the cultivar Surfinia Blue Violet.
2. Flowers of plants of the new *Petunia* were smaller than flowers of plants of the cultivar Surfinia Blue Violet.
3. Plants of the new *Petunia* had lighter colored flowers than plants of the Surfinia Blue Violet.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia*.

The photograph at the bottom of the sheet comprises a side perspective view of a typical flowering plant of 'MP201' grown in a container.

The photograph at the top of the sheet comprises a close-up view of typical leaves and flowers of 'MP201'.

DETAILED BOTANICAL DESCRIPTION

The aforementioned photographs and following observations and measurements describe plants grown in Lompoc, Calif., under commercial practice during the winter in a polycarbonate-covered greenhouse with day temperatures ranging from 21 to 24° C., night temperatures ranging from 15 to 18° C., and light levels ranging from 5,000 to 9,000 foot candles. Plants were grown for about 14 weeks with one plant per 10-cm container. Plants were pinched once about three weeks after planting. In the following description, color references are made to The Royal Horticultural Society Colour Chart, 1995 Edition, except where general terms of ordinary dictionary significance are used.

Botanical classification: *Petunia×hybrida* cultivar MP201.

Parentage:

*Female parent.*—Proprietary *Petunia* selection identified as X99.26.1, not patented.

*Male parent.*—Proprietary *Petunia* selection identified as X99.3.11, not patented.

Propagation:

*Type cutting.*—Vegetative cuttings.

*Time to initiate roots.*—About two weeks at 22° C.

*Time to develop roots.*—About three to four weeks at 22° C.

*Root description.*—Fine, fibrous; white in color.

*Rooting habit.*—Freely branching, dense.

Plant description:

*Form.*—Annual flowering plant; indeterminate; initially upright, then mounding and outwardly spreading; compact. Vigorous growth habit. Freely basal branching with about eight main lateral branches per plant with lateral branches potentially forming at every node.

*Usage.*—Appropriate for hanging baskets, window boxes, patio containers and landscape applications.

*Plant height.*—About 14 cm.

*Plant diameter.*—About 30 cm.

*Lateral branches.*—Length: About 23 cm. Diameter: About 2 mm. Internode length: About 1.5 cm. Texture: Pubescent. Color: 144A.

*Foliage description.*—Arrangement, before flowering: Alternate, simple. Arrangement, when flowering: Opposite, simple. Length: About 3.2 cm. Width: About 1.9 cm. Shape: Elliptical. Apex: Acute. Base: Attenuate. Margin: Entire. Texture, upper and lower surfaces: Glandular, viscid; pubescent. Venation pattern: Pinnate, arcuate. Color: Developing foliage, upper surfaces: Brighter than 146A. Developing foliage, lower surface: 146A. Fully expanded foliage, upper surface: Brighter than 146A. Fully expanded foliage, lower surface: 146B. Venation, upper surface: 146B. Venation, lower surface: 146C. Petiole length: About 1.2 cm. Petiole diameter: About 2 mm. Petiole texture, upper and lower surfaces: Sparsely pubescent. Petiole color, upper and lower surfaces: 146B.

Flower description:

*Flower type and habit.*—Small salverform flowers; flowers face upward or outward; single, axillary. Freely flowering, typically about eight open flowers per lateral stem.

*Natural flowering season.*—Long day responsive; spring until frost in the autumn; flowering continuous during the flowering period.

*Flower longevity on the plant.*—About one week; flowers persistent.

*Fragrance.*—None detected.

*Flower size.*—Diameter: About 4 cm. Tube length: About 3 cm. Throat diameter, distal end: About 8 mm. Tube diameter, proximal end: About 3 mm.

*Flower buds.*—Length: About 3 cm. Diameter: About 6 mm. Shape: Elongated oblong with ruffled apices. Color: 83B.

*Corolla.*—Arrangement/appearance: Single whorl of five petals, fused into flared trumpet with distinct clefts between petal lobes. Petal length from throat: About 1.8 cm. Petal width: About 2 cm. Petal shape: Roughly fan-shaped. Petal apex: Acute. Petal margin: Entire. Petal texture: Smooth, velvety. Color: Petal, upper surface, when opening: Brighter and more blue than 83A. Petal, lower surface, when opening: Slightly more gray than 83B. Petal, upper surface, fully opened: Brighter than 83B. Petal, lower surface, fully opened: 83C. Flower throat (inside): 79D. Flower tube (outside): 79B. Venation, upper and lower petal surfaces: 79A. Venation, throat: 79A. Venation, tube: 79B.

*Sepals.*—Arrangement/appearance: Single whorl of five sepals fused at base, star-shaped. Length: About 9 mm. Width: About 3.5 mm. Shape: Ligulate. Apex: Broadly acute. Margin: Entire. Texture, upper and lower surfaces: Glandular, viscid. Color, upper and lower surfaces: 146A.

*Peduncles.*—Length: About 2.5 cm. Width: About 1.25 mm. Angle: About 45° to the stem. Strength: Strong. Texture: Pubescent. Color: 144A.

*Reproductive organs.*—Stamens: Quantity/arrangement: Five, adnate to corolla tube. Anther shape: Ovoid. Anther length: About 2 mm. Anther color: 201B. Pollen amount: Moderate. Pollen color: 201B. Pistils: Quantity: One. Pistil length: About 2.1 cm. Stigma shape: Anvil-shaped; rounded. Stigma color: 147A. Style length: About 1.8 cm. Style color: 77C. Ovary color: 144A.

*Fruit/seed.*—Fruit and seed production has not been observed.

Disease/pest resistance: Plants of the new *Petunia* have not been noted to be resistant to pathogens and pests common to *Petunia*.

Garden performance: Plants of the new *Petunia* have been observed to have good garden performance and to be tolerant to rain, wind and temperatures ranging from −5 to 40° C.

It is claimed:

1. A new and distinct cultivar of *Petunia* plant named 'MP201', as illustrated and described.

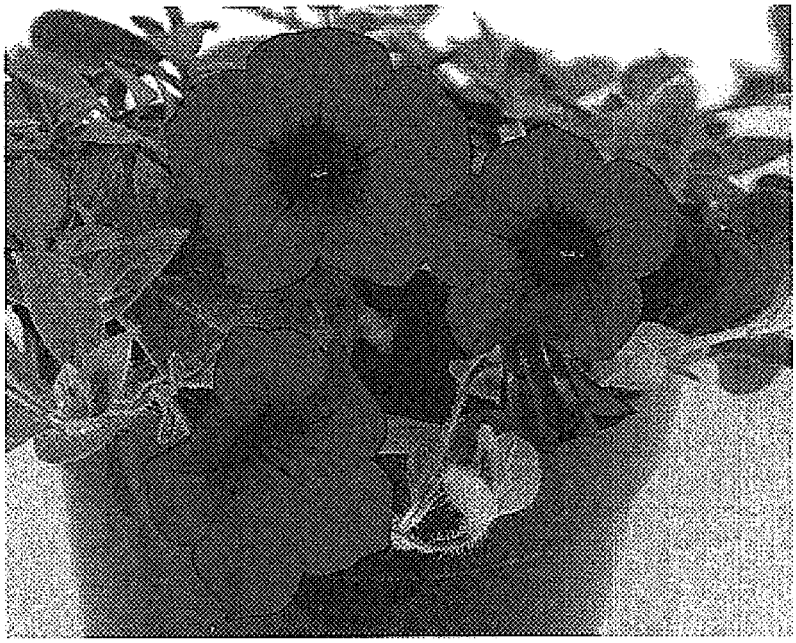
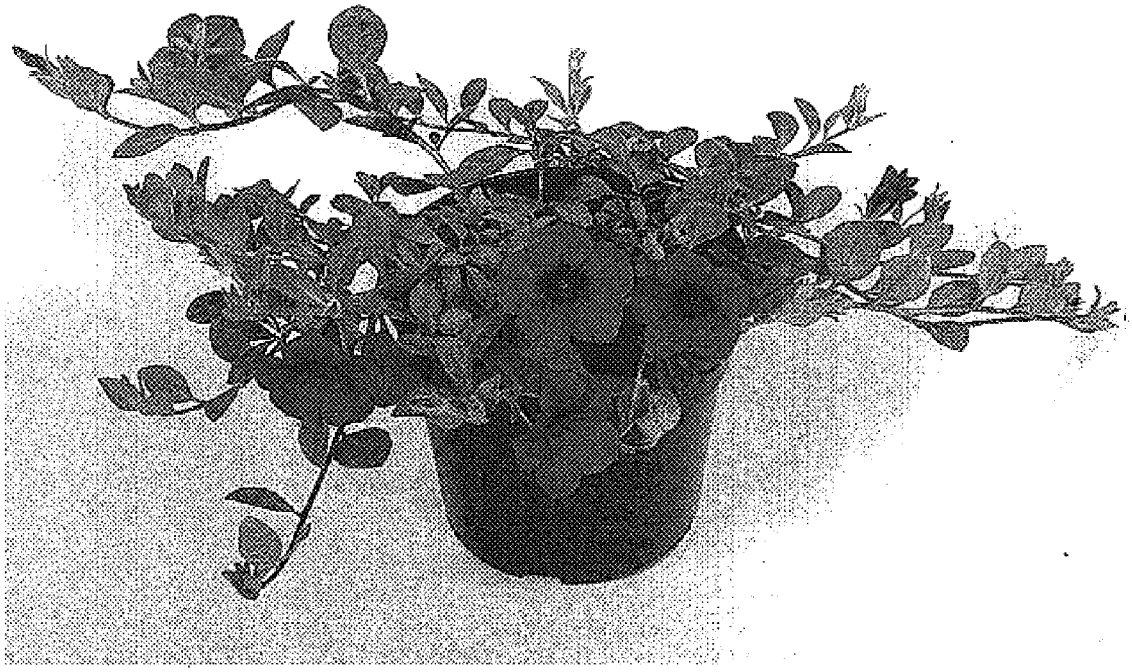

* * * * *